(12) United States Patent
Rückel

(10) Patent No.: US 6,238,897 B1
(45) Date of Patent: May 29, 2001

(54) CONTINUOUS PROCESS FOR PRODUCING 2-KETO-L-GULONIC ACID

(75) Inventor: Markus Rückel, Penzberg (DE)

(73) Assignee: Roche Vitamins Inc., Parsippany, NJ (US)

( * ) Notice: Subject to any disclaimer, the term of this patent is extended or adjusted under 35 U.S.C. 154(b) by 0 days.

(21) Appl. No.: 09/352,724

(22) Filed: Jul. 13, 1999

(30) Foreign Application Priority Data

Jul. 17, 1998 (EP) ................................................ 98113373

(51) Int. Cl.$^7$ ................................ C12P 7/60; C12P 1/04; C12P 39/00; C12N 1/20

(52) U.S. Cl. ............................ 435/138; 435/42; 435/170; 435/252.1

(58) Field of Search ............................... 435/42, 138, 170, 435/252.1

(56) References Cited

U.S. PATENT DOCUMENTS 5,312,741 * 5/1994 Hoshino et al. .

FOREIGN PATENT DOCUMENTS

| 0 518 136 A2 | 1/1993 | (EP) . |
| 1 120 249 | 7/1968 | (GB) . |
| WO 98/17819 | 4/1998 | (WO) . |

OTHER PUBLICATIONS

Campbell, "Biology," The Benjamin/Cummings Publishing Company, Inc., California, pp. 1113–1114, 1993.*

Crueger et al. "Biotechnology: A Textbook of Industrial Microbiology," Sinauer Associates, Inc. Massachusetts, pp. 67, 68, 97, 98, 1989.*

Tatsuo Hoshino, et al., Metabolic Pathway for 2–Keto–L–gulonic Acid Formation in *Gluconobacter melanogenus* IFO 0323, Agri. Biol. Chem., vol. 54 (5), 1211–1218 (1990).

Teruhide Sugisawa, et al., Microbial Production of 2–Keto–L–Gulonic Acid from L–Sorbose and D–Sorbitol by *Gluconobacter melanogenus*, Agri. Boil. Chem., vol. 54 (5), 1201–1209 (1990).

Tatsuo Hoshino, et al., Isolation and Characterization of NAD(P)–Dependent L–Sorbosone Dehydrogenase from *Gluconobacter melanogenus* UV10, Agri. Biol. Chem., vol. 55 (3), 655–670 (1991).

Teruhide Sugisawa, et al., Purification and Properties of NADPH–Linked L–Sorbose Reductase for *Gluconobacter melanogenus* N44–1, Agri. Biol. Chem., vol. 55 (8), 2043–2049 (1991).

Chemical Abstracts, vol. 1186, No. 21, abstract No. 212895, accession No. XP–002119882 (1992).

* cited by examiner

Primary Examiner—Francisco Prats
Assistant Examiner—Susan D. Coe
(74) Attorney, Agent, or Firm—Mark E. Waddell; Stephen M. Haracz; Bryan Cave LLP

(57) ABSTRACT

A process for the continuous production of 2-keto-L-gulonic acid or a salt thereof from D-sorbitol by fermentation with microorganisms in a nutrient medium containing D-sorbitol that is incubated in a first fermentation vessel with a microorganism capable of converting D-sorbitol to L-sorbose, whereafter the resulting fermentation broth containing L-sorbose is transferred to a second fermentation vessel where it is incubated with a microorganism capable of converting L-sorbose to 2-keto-L-gulonic acid. In a particularly preferred embodiment of this process, the fermentation broth from the first fermentation vessel is sterilized before being transferred to the second fermentation vessel. 2-keto-L-gulonic acid is a valuable intermediate for the production of vitamin C.

22 Claims, 1 Drawing Sheet

CONTINUOUS PROCESS FOR PRODUCING 2-KETO-L-GULONIC ACID

SUMMARY

The present invention relates to a continuous fermentation process for the manufacture of 2-keto-L-gulonic acid (2-KGA) from D-sorbitol. 2-KGA is a valuable intermediate for the production of ascorbic acid (vitamin C).

BACKGROUND OF THE INVENTION

Processes for the manufacture of 2-KGA from D-sorbitol are known. For example, EP 0 518 136 A2 discloses a fermentation process utilizing a mixed microorganism culture, whereby D-sorbitol is oxidized to L-sorbose with a microorganism belonging to the genus Gluconobacter or Acetobacter, e.g., *Glitcoitobacter suboxydans* IFO 3291, and the L-sorbose is in turn converted to 2-KGA by fermentation with the microorganism strain DSM 4025, also known as *Gluconobacter oxydans* DSM 4025. In this process both microorganisms coexist in the fermentation medium during at least part of the entire cultivation period. It has been found, however, that the yield in the process disclosed in EP 0 518 136 A2 is unsatisfactory when the process is carried out in continuous manner.

DETAILED DESCRIPTION OF THE INVENTION

Figure 1:
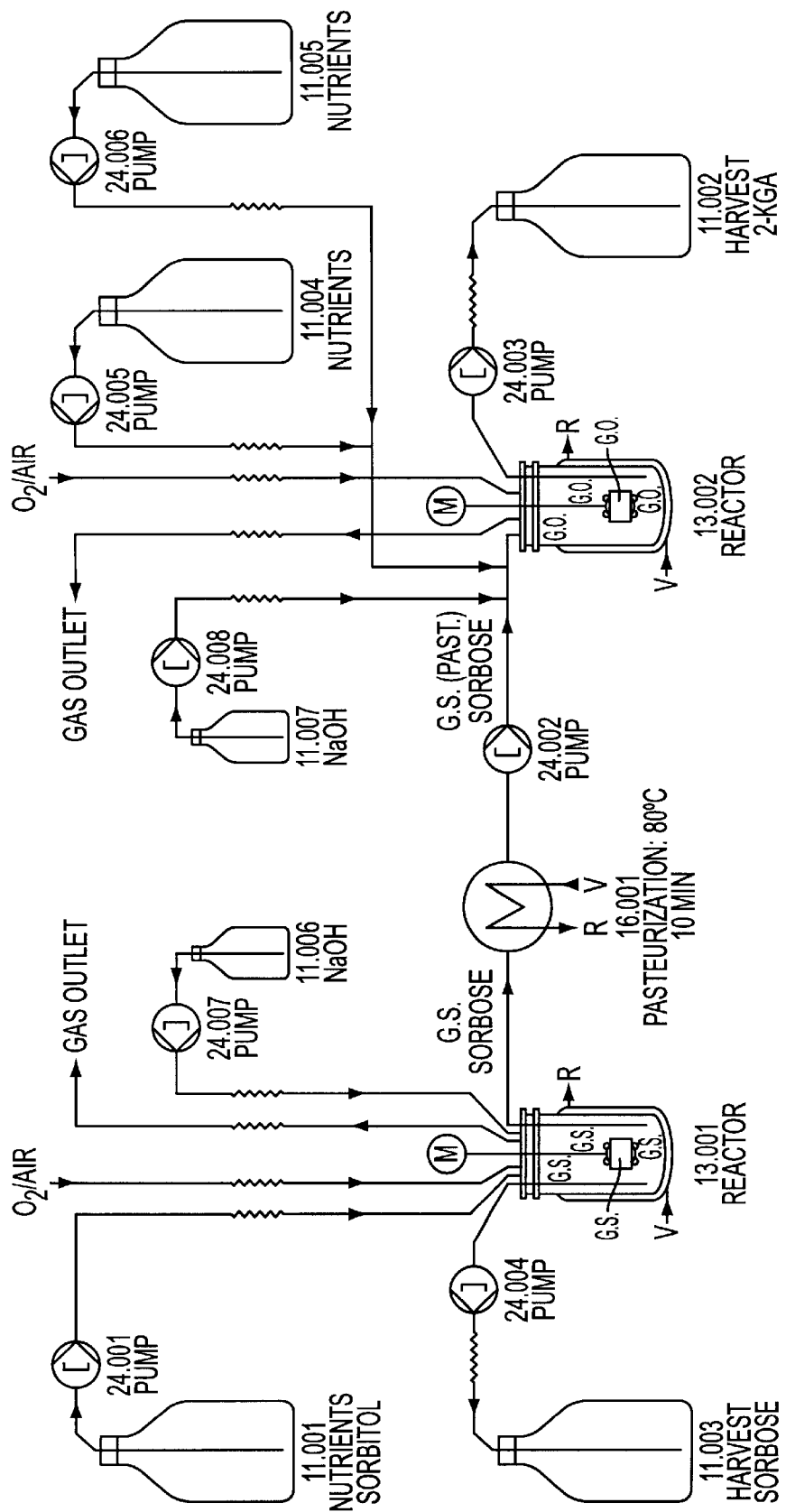
FIG. 1 shows a bioreactor system. The system has two fermentation vessels (reactor 13.001 (first fermentation vessel) and 13.002 (second fermentation vessel)), storage bottles 11.001, 11.004, and 11.005 for nutrient solutions, storage bottles 11.006 and 11.007 for 7.5M sodium hydroxide solution, harvest bottles 11.002 and 11.003 for harvesting 2-KGA and excess fermentation broth from reactor 13.001 (first fermentation vessel), a loop 16.001 for heating the fermentation broth and pumps 24.001, 24.002, 24.004, 24.005, 24.006, 24.007, and 24.008.

It is an object of the present invention to provide an efficient process for the manufacture of 2-KGA or a salt thereof from D-sorbitol in high yields; that minimizes losses from the formation of unwanted by-products, carbon dioxide and cell mass; and can be performed over an extended period of time without interruption, i.e., continuously.

Accordingly, the present invention provides a process for the continuous production of 2-KGA or a salt thereof from D-sorbitol by fermentation with microorganisms, in which process a nutrient medium containing D-sorbitol is incubated in a first fermentation vessel with a microorganism capable of converting D-sorbitol to L-sorbose, whereafter the resulting fermentation broth containing L-sorbose is transferred to a second fermentation vessel where it is incubated with a microorganism capable of converting L-sorbose to 2-KGA.

Examples of a microorganisms capable of converting D-sorbitol to L-sorbose are microorganisms of the genera Gluconobacter and Acetobacter, such as

*Gluconobacter suboxydans* IFO 3130, IFO 3255, IFO 3256, IFO 3257, IFO 3258, IFO 3289, IFO 3290 and IFO 3291;

*Gluconobacter gluconicus* IFO 3171, IFO 3285 and IFO 3286;

*Gluconobacter rubiginosus* IFO 3244;

*Gluconobacter albidus* IFO 3251 and IFO 3253;

*Gluconobacter industrius* IFO 3261;

*Gluconobacter cerinus* IFO 3262, IFO 3263, IFO 3265, IFO 3266, IFO 3267 and IFO 3270;

*Gluconobacter diacetonicus* IFO 3273;

*Gluconobacter roseus* IFO 3990;

*Acetobacter aceti* subsp. *orleans* IFO 3259;

*Acetobacter aceti* subsp. *aceti* IFO 3281;

*Acetobacter liquefaciens* IFO 12257, IFO 12258 and IFO 12388; and

*Acetobacter aceti* subsp. *xylinum* IFO 3288, IFO 13693, IFO 13772 and IFO 13773.

Preferred microorganisms are *Gluconobacter suboxydans* IFO 3255, 3256, 3258, 3290 and 3291; *Gluconobacter gluconicus* IFO 3285; and *Gluconobacter cerinus* IFO 3267. The most preferred microorganism is *Gluconobacter suboxydans* IFO 3291.

The above-named microorganisms are preserved in the public microorganism depositary (culture collection), The Institute of Fermentation Osaka, Japan (IFO), and are available to anyone upon request and payment of the requested fee.

The preferred microorganism for the conversion of L-sorbose to 2-KGA is *Gluconobacter oxydans* DSM 4025. This strain was deposited on Mar. 17, 1987 at the Deutsche Sammlung von Mikroorganismen in Göttingen, Germany (now located in Braunschweig), based on the stipulations of the Budapest Treaty, under DSM No. 4025. The depositor was The Oriental Scientific Instruments Import and Export Corporation for Institute of Microbiology, Academia Sinica, 52 San-Li-He Rd., Beijing, Peoples Republic of China. The effective depositor was said Institute, of which the full address is The Institute of Microbiology, Academy of Sciences of China, Haidian, Zhongguancun, Beijing 100080, People's Republic of China.

Regarding the nutrient medium suitable for the cultivation of the microorganisms used in the process of the invention, although no special restrictions are imposed, an aqueous nutrient medium may include carbon sources and nitrogen sources. Other inorganic salts, small amounts of other nutrients and the like, which can be utilized by the microorganisms, are desirable for the advantageous incubation of the microorganisms. Various nutrient materials that are generally used for the better growth of microorganisms may suitably be included in the medium.

In addition to the D-sorbitol, which is used as the starting material in the process of the present invention, other substances that are carbon sources may also be present in the nutrient medium, such as glycerol, D-glucose, D-mannitol, D-fructose, D-arabitol and the like.

Various organic or inorganic substances may also be used as nitrogen sources in the process, such as meat extract, peptone, casein, corn steep liquor, urea, amino acids, nitrates, ammonium salts and the like. Magnesium sulfate, potassium phosphate, ferrous and ferric chlorides, calcium carbonate and the like may be used as inorganic substances.

The mixing ratio of these nutrients and the amounts of each ingredient may vary with the generic properties of the microorganisms employed, the amounts of the starting material, D-sorbitol, the amount of one of the microorganisms to be inoculated with respect to the other and the times of inoculations, and the other conditions of the incubation may be selected or determined in accordance with the particulars of the individual case.

The suitable concentration of the starting material, D-sorbitol, in the medium contained in the first fermentation vessel depends on the generic character and the like of the employed microorganism in any instance. In a preferred embodiment, the concentration of D-sorbitol in the nutrient medium in the first fermentation vessel is from about 10 to about 400 g/l, more preferably from about 150 to about 350 g/l. The concentration of L-sorbose, produced in the first fermentation vessel, in the fermentation broth fed to the second fermentation vessel is preferably from about 5 to about 200 g/l, more preferably from about 60 to about 180 g/l.

The further conditions of the fermentation (cultivation) may also vary depending on the species and generic character of the particular microorganisms employed. The composition of the medium may, of course, be selected or determined in accordance with the particulars of the individual case in order to yield the intended product most efficiently. In the first fermentation vessel, the cultivation temperatures are suitably from about 12 to about 38° C., preferably from about 18 to about 32° C., and in the second fermentation vessel, the cultivation temperatures are suitably from about 20 to about 33° C. In the first fermentation vessel, the pH value of the medium is suitably from about 2.0 to about 9.0, preferably from about 3.0 to about 7.0. In the second fermentation vessel, the pH of the broth is suitably from about 5.0 to about 9.0, preferably from about 6.0 to about 8.0.

In a further preferred aspect of the process of the invention, the fermentation is carried out at a dissolved oxygen concentration of from about 0.1 to about 200% air saturation, preferably of from about 5 to about 100% air saturation, in the first fermentation vessel; and of from about 8 to about 80% air saturation in the second fermentation vessel.

Furthermore, the fermentation is preferably carried out at oxygen concentrations in the gassing flow of from about 0.1 to about 100%, preferably of from about 15 to about 100%, in the first fermentation vessel, and of from about 19 to about 100% in the second fermentation vessel; and at gassing rates of from about 0.01 to about 1.2 v./v./min. (volume of gas per volume of reactor per minute) in the first fermentation vessel, and of from about 0.03 to about 0.85 v./v./min. in the second fermentation vessel.

It is also preferred to carry out the fermentation in the first fermentation vessel at dilution rates of liquid flow of about 0.02 to about 0.5 $h^{-1}$, more preferably of about 0.06 to about 0.3 $h^{-1}$. The dilution rate of liquid flow in the second fermentation vessel is preferably about 0.03 to about 0.25 $h^{-1}$.

While the fermentation according to the present invention may be carried out at normal pressure, i.e., at about 1 bar, it is generally preferred to work under elevated pressure, e.g., a pressure of at least 3 bar, most preferably at least 5 bar.

In a particular, a preferred embodiment of the process of the present invention the fermentation broth from the first fermentation vessel is sterilized before being transferred to the second fermentation vessel. This sterilization can be achieved by heating the fermentation broth in the first fermentation vessel before being transferred to the second fermentation vessel to a temperature of about 35 to about 121° C., preferably of from 45 to 80° C., or by effecting the heating to such a temperature after the fermentation broth has been removed (discharged) from the first fermentation vessel but before it has been introduced into the second, i.e., during the passage from the first to the second fermentation vessel.

In a further particularly preferred embodiment of the process of the present invention, nutrient medium containing D-sorbitol is fed to the first fermentation vessel at a rate higher than the rate at which the fermentation broth containing L-sorbose is transferred from the first fermentation vessel to the second fermentation vessel, while simultaneously part of the fermentation broth containing the produced L-sorbose is discharged film the first fermentation vessel into a separate vessel, thereby keeping the volume of fermentation broth in the first fermentation vessel substantially constant.

In another particularly preferred embodiment of the process of the present invention, nutrient medium is fed into the second fermentation vessel during the fermentation process. The supply rate of nutrient medium to the second fermentation vessel is adjusted to the supply rate of fermentation broth from the first fermentation vessel and to the discharge rate of fermentation broth from the second fermentation vessel, so that the working volume in the second fermentation vessel is kept substantially constant. The nutrient medium supplied to the second fermentation vessel is suitably substantially the same as the nutrient medium used in the first fermentation vessel except that it contains no sorbitol. In a preferred embodiment, nutrient media of different composition in respect to the nutrients and their concentration are supplied from separate storage containers to the second fermentation vessel at variable rates in order to enable the establishment of optimal conditions for the growth of the microorganism in the fermentation broth.

In order to optimize the yield of the process, the fermentation can be carried out by using more than one fermentation vessel in each step of the entire process. For example, the fermentation of D-sorbitol to L-sorbose and/or the fermentation of L-sorbose to 2-KGA can be carried out in two or more fermentation vessels that are positioned in consecutive or parallel order.

Suitably, the microorganism in each fermentation vessel is partially or totally immobilized by methods known per se, such as chemical bonding, e.g., covalent or ionic bonding, crosslinking with polymers, or physical methods for cell retention, e.g., adsorptive bonding, matrix entrappment, microencapsulation or by use of membrane reactors, or combination of such immobilization methods. In a preferred embodiment, the microorganisms are immobilized by cell adhesion to porous organic carriers, e.g., polymers such as cellulose; or inorganic carriers, e.g., minerals such as bentonite or steatite, ceramics or glass beads.

In order to maintain the pH value of the medium to that most suitable for the enzymatic activity, any suitable acidic or basic agent may be added to the medium in a suitable amount at a suitable time during the cultivation. The same object may alternatively be accomplished by initially incorporating a suitable buffer or buffering agent into the medium at the beginning of the cultivation.

The 2-keto-L-gulonic acid thus produced in the second fermentation vessel may be separated and purified by conventional methods known per se, and it may be separated as a salt, e.g., of sodium, potassium, calcium, ammonium or the like if the corresponding metal ions are present in the fermentation (nutrient) medium; this is the case when inorganic salts of sodium, potassium, calcium, ammonium, etc. are present. The salt may be converted into the free acid by conventional methods known per se.

The invention is illustrated further by the following Examples, in which the percentages are expressed on the basis of weight/volume.

EXAMPLE 1

Preparation of Seed Cultures (a) An aqueous seed medium for use in the first fermentation vessel containing 10% of D-sorbitol, 0.006% of yeast extract, 0.02% of magnesium sulfate heptahydrate, 1% of corn steep, 0.03% of potassium dihydrogen phosphate and 0.06% of calcium carbonate was prepared.

One loopful of *Gluconobacter suboxydans* IFO 3291 was transferred into 300 ml of the seed medium in a 1 l shaking flask. The flask was incubated at 28° C. with shaking for 2 days.

(b) An aqueous seed medium for use in the second fermentation vessel containing 4% of L-sorbose, 0.5% of urea, 0.05% of glyceride, 0.25% of magnesium sulfate heptahydrate, 1.75% of corn steep, 5% of yeast extract and 1.5% of calcium carbonate was prepared. Five loopfuls of *Gluconobacter oxydans* DSM 4025 were transferred into 300 ml of the seed medium in a 1 l shaking flask. The flask was incubated at 28° C. with shaking for 3 days.

EXAMPLE 2

A bioreactor system as shown FIG. 1 was assembled. The system had two fermentation vessels (reactor 13.001 (first fermentation vessel) and 13.002 (second fermentation vessel)), storage bottles 11.001, 11.004 and 11.005 for nutrient solutions, storage bottles 11.006 and 11.007 for 7.5 M sodium hydroxide solution, harvest bottles 11.002 and 11.003 for harvesting 2-KGA and excess fermentation broth from reactor 13.001 (first fermentation vessel), a loop 16.001 for heating the fermentation broth and pumps 24.001, 24.002, 24.003, 24.004, 24.005, 24.006, 24.007 and 24.008.

Storage bottle 11.001 contained an aqueous solution with 11.5% of D-sorbitol, 1% of corn steep powder, 0.006% of magnesium sulfate heptahydrate, 0.03% of potassium dihydrogen phosphate and 0.06% of calcium carbonate.

Storage bottle 11.004 contained an aqueous solution with 20% of corn steep powder, 0.03% of magnesium sulfate heptahydrate, 0.03% of potassium dihydrogen phosphate and 0.06% of calcium carbonate.

Storage bottle 11.005 contained an aqueous solution with 1% yeast extract, 0.03% of magnesium sulfate heptahydrate, 0.03% of potassium dihydrogen phosphate and 0.06% of calcium carbonate.

The fermentation vessels were equipped with gas supply and a stirrer. A spinning basket was fixed to both stirrer shafts of the fermentation vessels (13.001 and 13.002). The baskets were filled with spherical porous ceramic carrier material having a mean pellet diameter of about 3.5 $\mu$m and a mean pore diameter of about 100 mm (Ceramtec AG, Marktredwitz, Germany).

EXAMPLE 3

The bioreactor system as described in Example 2, with reference to FIG. 1, was put into operation by the following consecutive steps:

1. Assembly of all parts of the reactors, pumps, tubes and instrumentation.
2. Autoclaving at 121° C. for 20 minutes in suitable partitions.
3. Preparation of culture broth for continuous operation by dosing the components by weight to the storage bottles and autoclaving (121° C., 20 minutes).
4. Connecting reactors, caustic, storage and harvest bottles under sterile conditions.
5. Charging reactor 13.001 (total volume 2 liters) with 600 ml of the seed medium described in Example 1(a) under sterile conditions. pH=6.8, temperature=18° C., dissolved oxygen (DO) concentration=2%$_{air}$, total pressure ($P_{tot}$)=1.1 bar, and partial pressure of oxygen ($Po_2$)=0.6 bar
6. Because of oxygen consumption mainly from the conversion of sorbitol to sorbose and the evolution of $CO_2$, the stirrer speed of the reactor was raised until a constant value of the DO concentration of 2% was maintained. When the sorbitol was substantially consumed, the DO concentration increased due to decrease of oxygen consumption by the microorganism, thereby triggering the next step.
7. Switching on pump 24.001 for educt supply at 151 ml/h.
8. Charging reactor 13.002 (total volume of 2 liters) with 450 ml of the seed medium described in Example 1(b) under sterile conditions. pH=7.0, temperature=28° C., DO concentration=10%$_{air}$, $P_{tot}$=1.1 bar, and $Po_2$=0.52 bar.
9. Switching on pump 24.002 for transferring broth from reactor 13.001 to reactor 13.002 at 33 ml/h, pump 24.004 (1.8 ml/h) and pump 24.005 for additional nutrient supply (2 ml/h). The residual sorbose broth was transferred to harvest bottle 11.003. The broth containing 2-keto-L-gulonic acid was harvested in bottle 11.002.
10. Analysis of concentrations of sorbitol, sorbose and 2-keto-L-gulonic acid was effected by high performance liquid chromatography.

Finally, the process was operated continuously in stationary phase under the conditions given in the following overview:

TABLE 1

Process conditions in reactor 13.001:
pH was controlled with 7.5 M NaOH
Total sorbitol concentration (inlet): 113.1 g/kg (119.9 g/l)

| pH [−] | 6.8 | Sorbose [g/l] | 103.7 |
|---|---|---|---|
| T [° C.] | 18 | Sorbose [g/kg] | 97.8 |
| DO [% air] | 2 | D [1/h] | 0.126 |
| $P_{tot}$ [bar] | 1.1 | Gassing rate [min$^{-1}$] | 0.36 |
| $Po_2$ [bar] | 0.6 | $V_{reactor}$ [l] | 1.2 |
| $OD_{660}$ | 8.45 | CCD [ml$^{-1}$] | 7.4$^9$ |

D : dilution rate
OD : optical density (at 660 nm)
CCD : counted cell density
Gassing rate : volume of gas stream per reactor volume per minute
$V_{reactor}$ : working volume of the reactor

TABLE 2

Process conditions in reactor 13.002:
pH was controlled with 7.5 M NaOH
Total $C_6$ - monosaccharide concentration (inlet): 85.6 g/kg (90.7 g/l)

| pH [−] | 7.0 | 2-KGA [g/l] | 89.5 |
|---|---|---|---|
| T [° C.] | 28 | 2-KGA [g/kg] | 84.4 |
| DO [% air] | 10 | D [1/h] | 0.045 |
| $P_{tot}$ [bar] | 1.1 | Gassing rate [vvm] | 0.1 |
| $Po_2$ [bar] | 0.52 | $V_{reactor}$ [l] | 0.9 |
| $OD_{660}$ [−] | 18.2 | CCD [1/ml] | 2$^{10}$ |

TOTAL SYSTEM

Total sorbitol concentration (reactor 13.001): 113.1 g/kg (119.9 gl) Dilution factor of broth between reactor 13.001 and reactor 13.002: 0.82

TABLE 3

Summary results for reactor 13.001 and reactor 13.002:

| | |
|---|---|
| Overall yield [% wt] | 91 |
| Overall yield [% mol] | 85.5 |
| Productivity [g/l/h]: | 3.1 |

What is claimed is:

1. A process for the continuous production of 2-keto-L-gulonic acid or a salt thereof from D-sorbitol by fermentation with microorganisms, comprising incubating a nutrient medium containing D-sorbitol in a first fermentation vessel with a microorganism capable of converting D-sorbitol to L-sorbose, whereafter the resulting fermentation broth containing L-sorbose is sterilized and subsequently transferred to a second fermentation vessel where it is incubated with a microorganism capable of converting L-sorbose to 2-keto-L-gulonic acid.

2. The process according to claim 1, wherein the sterilization is carried out by heating the fermentation broth in the first fermentation vessel before being transferred to the second fermentation vessel to a temperature of about 35 to about 121° C. or heating to such a temperature after the fermentation broth has been removed from the first fermentation vessel but before it has been introduced into the second fermentation vessel.

3. The process according to claim 2, wherein the sterilization temperature is about 45 to 80° C.

4. The process according to claim 1, wherein the nutrient medium is fed to the first fermentation vessel at a rate higher than the rate at which the fermentation broth is transferred from the first fermentation vessel to the second fermentation vessel and the fermentation broth is discharged from the first fermentation vessel into a separate vessel in sufficient quantity to keep the volume of fermentation broth in the first fermentation vessel about constant.

5. The process according to claim 1, wherein nutrient medium is fed into the second fermentation vessel during the fermentation process and the supply of nutrient medium to the second fermentation vessel is adjusted to the rate of supply of fermentation broth from the first fermentation vessel and to the rate of discharge of fermentation broth from the second fermentation vessel, so that the working volume in the second fermentation vessel is kept about constant.

6. The process according to claim 1, wherein the microorganism capable of converting D-sorbitol to L-sorbose is a microorganism of the genus Gluconobacter or Acetobacter.

7. The process according to claim 6, wherein the microorganism is from the genus Gluconobacter.

8. The process according to claim 7, wherein the microorganism is *Gluconobacter suboxydans* IFO 3291.

9. The process according to claim 1, wherein the microorganism capable of converting L-sorbose to 2-keto-L-gulonic acid is *Gluconobacter oxydans* DSM 4025.

10. The process according to claim 1, wherein the concentration of D-sorbitol in the nutrient medium in the first fermentation vessel is from about 10 to about 400 g/l.

11. The process according to claim 10, wherein the concentration of D-sorbitol in the nutrient medium in the first fermentation vessel is from about 150 to about 350 g/l.

12. The process according to claim 1, wherein the concentration of L-sorbose in the fermentation broth fed to the second fermentation vessel is about 5 to about 200 g/l.

13. The process according to claim 12, wherein the concentration of L-sorbose in the fermentation broth fed to the second fermentation vessel is about 60 to about 180 g/l.

14. The process according to claim 1, wherein the fermentation is carried out in the first fermentation vessel at a temperature of about 12 to about 38° C. and in the second fermentation vessel at a temperature of about 20 to about 33° C.

15. The process according to claim 14, wherein the fermentation is carried out in the first fermentation vessel at a temperature of about 18 to about 32° C.

16. The process according to claim 1, wherein the fermentation is carried out in the first fermentation vessel at a pH value of about 2.0 to about 9.0 and in the second fermentation vessel at a pH value of about 5.0 to about 9.0.

17. The process according to claim 16, wherein the fermentation is carried out in the first fermentation vessel at a pH value of about 3.0 to about 7.0 and in the second fermentation vessel at a pH value of about 6.0 to about 8.0.

18. The process according to claim 1, wherein the fermentation is carried out at a dissolved oxygen concentration of about 0.1 to about 200% air saturation in the first fermentation vessel and of about 8 to about 80% air saturation in the second fermentation vessel.

19. The process according to claim 18, wherein the fermentation is carried out at a dissolved oxygen concentration of about 5 to about 100% air saturation in the first fermentation vessel.

20. The process according to claim 1, wherein the fermentation is carried out at oxygen concentrations in the gassing flow of about 0.1 to about 100% in the first fermentation vessel and of from about 19 to about 100% in the second fermentation vessel.

21. The process according to claim 20, wherein the fermentation is carried out at oxygen concentrations in the gassing flow of about 15 to about 100% in the first fermentation vessel.

22. The process according to claim 1, wherein the fermentation is carried out at gassing rates of about 0.01 to about 1.2 v./v./min. in the first fermentation vessel and of about 0.03 to about 0.85 v./v./min. in the second fermentation vessel.

* * * * *

UNITED STATES PATENT AND TRADEMARK OFFICE
CERTIFICATE OF CORRECTION

PATENT NO. : 6,238,897
DATED : July 13, 1999
INVENTOR(S) : Markus Rückel

Page 1 of 1

It is certified that error appears in the above-identified patent and that said Letters Patent is hereby corrected as shown below:

Title page,
Item [56] References Cited, OTHER PUBLICATIONS, in the fourth listed reference (Teruhide Sugisawa, et al.), please change "Boil." to -- Biol. --;

Column 7,
Line 47, please italicize "Gluconobacter" and "Acetobacter;" and
Line 49, please italicize "Gluconobacter."

Signed and Sealed this

Fifteenth Day of January, 2002

Attest:

Attesting Officer

JAMES E. ROGAN
*Director of the United States Patent and Trademark Office*